(12) United States Patent
Emmrich et al.

(10) Patent No.: US 8,986,743 B2
(45) Date of Patent: Mar. 24, 2015

(54) ANIMAL MODEL FOR THE HUMAN IMMUNE SYSTEM, AND METHOD FOR PRODUCING THE SAME

(75) Inventors: Frank Emmrich, Leipzig (DE); Manja Kamprad, Leipzig (DE); Manuela Ackermann, Leipzig (DE)

(73) Assignee: Universität Leipzig, Leipzig (DE)

( * ) Notice: Subject to any disclaimer, the term of this patent is extended or adjusted under 35 U.S.C. 154(b) by 1100 days.

(21) Appl. No.: 11/914,649

(22) PCT Filed: May 17, 2006

(86) PCT No.: PCT/DE2006/000893
§ 371 (c)(1),
(2), (4) Date: Nov. 16, 2007

(87) PCT Pub. No.: WO2006/122545
PCT Pub. Date: Nov. 23, 2006

(65) Prior Publication Data
US 2008/0216182 A1    Sep. 4, 2008

(30) Foreign Application Priority Data

May 17, 2005 (DE) .......................... 10 2005 023 342

(51) Int. Cl.
*A61K 35/28* (2006.01)
*C12P 21/00* (2006.01)
*A01K 67/00* (2006.01)
*A01K 67/027* (2006.01)

(52) U.S. Cl.
CPC ..... *A01K 67/0271* (2013.01); *A01K 2267/0381* (2013.01)
USPC .................................. 424/577; 800/9; 800/21

(58) Field of Classification Search
CPC .................. A01K 67/0271; A01K 2267/0381; A01K 227/105
USPC .......................................... 424/577; 800/8, 21
See application file for complete search history.

(56) References Cited

U.S. PATENT DOCUMENTS

2003/0180269 A1* 9/2003 Hariri .......................... 424/93.21

FOREIGN PATENT DOCUMENTS

DE    4337007    * 12/1994
WO    01/15521 A1    3/2001

OTHER PUBLICATIONS

Verstegen MM et al., Transplantation of human umbilical cord blood cells in macrophage-depleted SCID mice: evidence for accessory cell involvement in expansion of immature CD34+CD38-cells Blood. Mar. 15, 1998;91(6):1966-76.*

Potian et alJ Immunol. Oct. 1, 2003;171(7):3426-34. Veto-like activity of mesenchymal stem cells: functional discrimination between cellular responses to alloantigens and recall antigens.*
Liles et a., Review: Nomenclature and Biologic Significance of Cytokines Involved in Inflammation and the Host Immune response the Journal of Infectious Diseases, vol. 172, No. 6 (Dec. 1995), pp. 1573-1580.*
Liu et al., Cytokine interactions in mesenchymal stem cells from cord bloodCytokine vol. 32, Issue 6, Dec. 21, 2005, pp. 270-279.*
Mosier et al.,Nature. Sep. 15, 1988;335(6187):256-9.Transfer of a functional human immune system to mice with severe combined immunodeficiency. Abstract.*
Leukocyte—definition of leukocyte in the Medical dictionary—by the Free Online Medical last visited Jan. 29, 2014.*
Transfer of a functional human immune system to mice with severe combined immunodeficiency Nature 335, 256-259 (Sep. 15, 1988).*
Theise et al .,Experimental Hematology 30 (2002) 1333-1338 I Society for Experimental Hematology. Radiation pneumonitis in mice: A severe injury model for pneumocyte engraftment from bone marrow.*
Kuci et al 2009 Adult Stem Cells as an Alternative Source of Multipotential (Pluripotential) Cells in Regenerative Medicine Current Stem Cell Research & Therapy pp. 107-117.*
Shulz et al., Humanized mice in translational biomedical research Nature Reviews Immunology 7, 118-130 (Feb. 2007).*
Bonnet D et al.: "Cytokine treatment or accessory cells are required to initiate engraftment of purified primitive human hematopoietic cells transplanted at limiting doses into NOD/SCID mice,"; Bone Marrow Transplantation Feb. 1999, vol. 23, No. 3, pp. 203-209—see attached international search report.
Cashman J D et al.: "Human growth factor-enhanced regeneration of transplantable human hematopoietic stem cells in nonobese diabetic/severe combined immunodeficient mice"; Blood, W.B. Saunders, Philadelphia, VA, USA, vol. 93, No. 2, Jan. 15, 1999, pp. 481-487—see attached international search report.
Lapido T et al.: "Cytokine stimulation of multilineage hemtopoiesis from immature human cells engrafted in SCID mice"; Science, American Association for the Advancement of Science, USA vol. 255, No. 5048, Feb. 28, 1992, pp. 1137-1141—see attached international search report.
Nobuyoshi Masaharu et al.: "Arrest of human dendritic cells at the CD34-/CD4*/HLA-DR+ stage in the bone marrow of NOD/SCID human chimeric mice"; Blood, vol. 97, No. 11, Jun. 1, 2001, pp. 3655-3657—see attached international search report.
Tornell J, Snaith M.; Transgenic systems in drug discovery: from target identification to humanized mice. Drug Discovery Today 2002; 7(8):461-470.
Bolon B.; Genetically engineered animals in drug discovery and development: A maturing resource for toxicologic research. Basic & Clinical Pharmacology & Toxicology 2004; 95(4):154-161.

(Continued)

*Primary Examiner* — Maria Leavitt
(74) *Attorney, Agent, or Firm* — Gudrun E. Huckett

(57) ABSTRACT

In a method for preparing an animal model for the human immune system in a non-human mammal, human stem cells with hematopoietic potential are transplanted into a non-human mammal. The non-human mammal is conditioned with cell culture supernatant of a culture of human cell lines, cells and/or tissue. The cell culture supernatant is derived from cell lines producing cytokines and other molecular mediators.

8 Claims, 11 Drawing Sheets

(56) References Cited

OTHER PUBLICATIONS

Igney FH, Asadullah K, Zollner TM.; Techniques: Species' finest blend—humanized mouse models in inflammatory skin disease research. Trends in Pharmacological Sciences 2004; 25(10):543-549.

Traggiai E, Chicha L, Mazzucchelli L, Bronz L, Piffaretti JC, Lanzavecchia A et al.; Development of a human adaptive immune system in cord blood cell-transplanted mice. Science 2004; 304(5667):104-107.

Kollet O, Peled A, Byk T, Ben Hur H, Greiner D, Shultz L et al.; beta 2 microglobulin-deficient (B2m(null)) NOD/SCID mice are excellent recipients for studying human stem cell function. Blood 2000; 95(10):3102-3105.

Rossi MID, Medina KL, Garrett K, Kolar G, Comp PC, Shultz LD et al.; Relatively normal human lymphopoiesis but rapid turnover of newly formed B cells in transplanted nonobese diabetic/SCID mice. Journal of Immunology 2001; 167(6):3033-3042.

Kolar GR, Yokota T, Rossi MID, Nath SK, Capra JD.; Human fetal, cord blood, and adult lymphocyte progenitors have similar potential for generating B cells with a diverse immunoglobulin repertoire. Blood 2004; 104 (9):2981-2987.

Samira S, Ferrand C, Peled A, Nagler A, Tovbin Y, Ben Hur H et al.; Tumor Necrosis Factor Promotes Human T-Cell Development in Nonobese Diabetic/Severe Combined Immunodeficient Mice. Stem Cells 2004; 22 (6):1085-1100.

Vallet V, Mauray S, Kindler V, Aubry D, Ruegg M, Cherpillod J et al.; Human tonsil implants xenotransplanted in SCID mice display broad lymphocytic diversity and cellular activation profile similar to those in the original lymphoid organ. Xenotransplantation 2005; 12(1):38-48.

Nobuyoshi M, Kusunoki Y, Seyama T, Kodama K, Kimura A, Kyoizumi S.; Arrest of human dendritic cells at the CD34(-)/CD4(+)/HLA-DR+ stage in the bone marrow of NOD/SCID-human chimeric mice. Blood 2001; 97 (11):3655-3657.

Cravens PD, Melkus MW, Padgett-Thomas A, Islas-Ohlmayer M, del M, Garcia JV.; Development and activation of Human Dendritic Cells in Vivo in a Xenograft Model of Human Hematopoiesis. Stem Cells 2005; 23 (2):264-278.

Shultz LD et al.; Human lymphoid and myeloid cell development in NOD/LtSz-scid IL2R gamma null mice engrafted with mobilized human hemopoietic stem cells; Journal of Immunology, Vol. 174, May 15, 2005; pp. 6477-6489.

Kerre T et al.; Adapted NOD/SCID model supports development of phenotypically and functionally mature T cells from human umbilical cord blood CD34(+) cells; vol. 99; 2002, pp. 1620-1626; XP003013883.

Vormoor J et al.; Immature human cord blood progenitors engraft and proliferate to high levels in severe combined immunodeficient mice; vol. 83, 1994; pp. 2489-2497; XP000574284.

Kollmann et al.; Reconstitution of SCID mice with human lymphoid and myeloid cells after transplantation with human fetal bone marrow without the requirement for exogenous human cytokines; PNAS; vol. 91; 1994; pp. 8032-6036.

Dao M A et al.: "Immunodeficient mice as models of human hematopoietic stem cell engraftment"; Current Opinion in Immunology, Current Biology Ltd., vol. 11, No. 5, Oct. 1, 1999, pp. 532-537.

\* cited by examiner

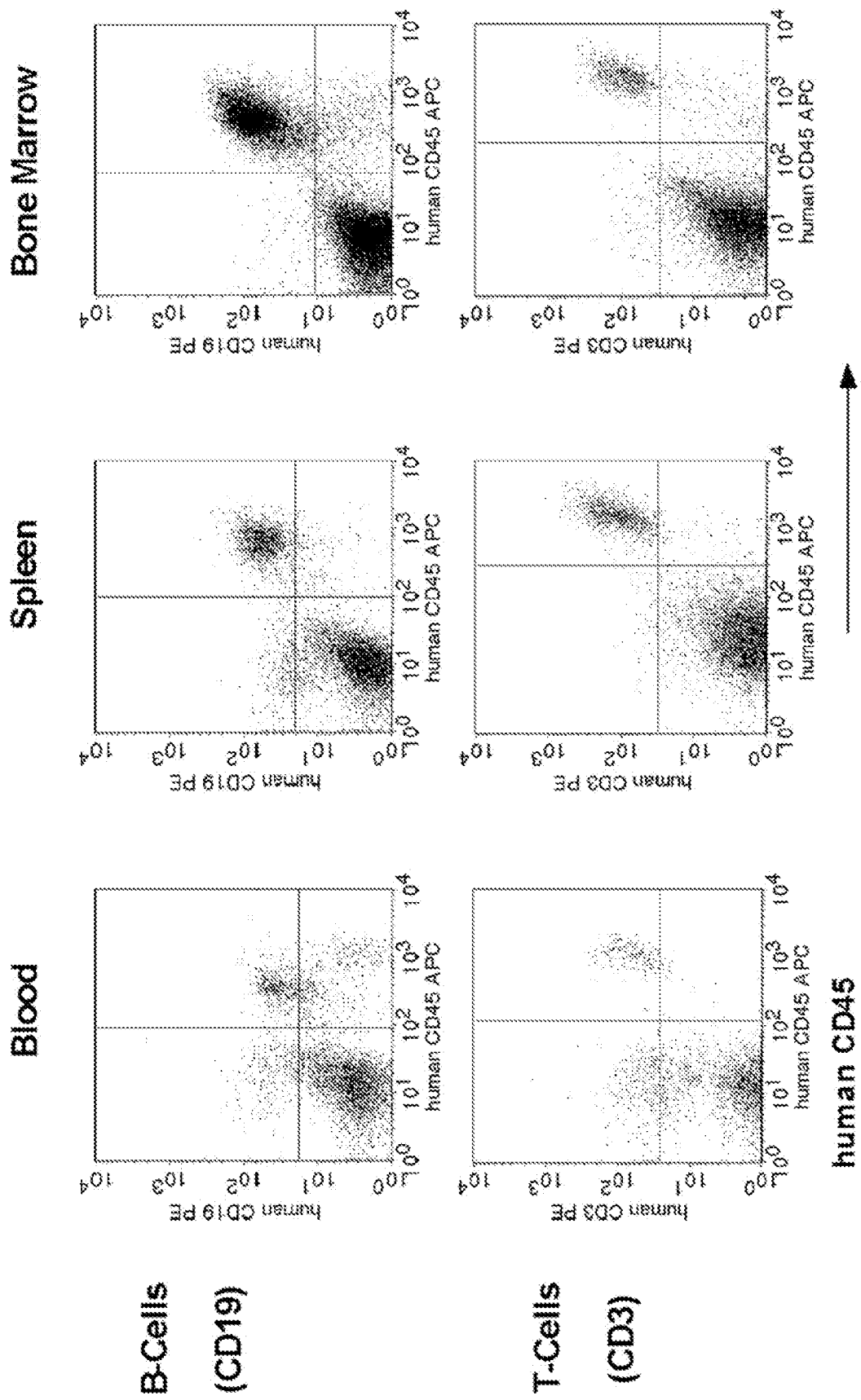

ANIMAL MODEL FOR THE HUMAN IMMUNE SYSTEM, AND METHOD FOR PRODUCING THE SAME

BACKGROUND OF THE INVENTION

The present invention relates to a method for establishing a functional adaptive human immune system in a suitable animal model as well as to an animal model produced by the method. The animal model is suitable, for example, for pre-clinical pharmacological studies and the production of human antibodies. Preferably, immunodeficient mice can be used for this purpose that develop hardly any immunological reactions with regard to the transplanted cells.

Basic strategies and technologies of a medical therapy in particular in the field of regenerative medicine are often characterized in animal models (for example, by employing rodents). When applying the principles derived in this way in a clinical application on humans it is often difficult to delimit whether a therapeutic product or a therapeutic strategy is optimal or not for a human target. There are thus two possibilities: a) the human target is invalid in the clinical application or b) the therapeutic agent does not have the same functional properties. This is especially relevant for tumor and transplantation therapies (inter alia, stem cell transplantations) and with particular attention in immune therapies that utilize species-specific monoclonal or polyclonal antibody preparations. Pharmaceutical companies are confronted with the challenge that only 10% of the active ingredients tested in clinical studies will result in a new approved medication. For verifying as well as accepting a new technology or working strategy, pre-clinical models and tools are required in which human cells and tissue ran be examined in a system-biological context that is as complex as possible. Immunodeficiency mice in which human cells of the immune system react with one another without being rejected can provide an answer in this connection because they combine the advantage of a small animal model with an improved correlation to the clinical conditions. Two strategies for developing corresponding animal models in rodents have been realized up to now.

The first strategy utilizes the technology for producing genetically modified (transgenic, knock-out, knock-in) animals by means of introduction of human genes, by induction of specific mutations or the replacement of a murine gene by the homolog human gene in somatic cells or germ cells in order to imitate genetic modifications or in order to express human antigens or targets. The limits of this method, in addition to the high costs and the minimal rate of success, lie in particular in the limited production of usually single human properties and thus their reactivity usually with animal partner molecules as well as usually with non-identical gene expression control mechanisms. Therefore, this method is usually exclusively used for characterization of the potential of active ingredients with regard to active ingredient metabolism and the determination of toxicity or for the examination of activity of an individual target or a set of targets (1; 2).

The second and more complex path is the generation of chimeras by xeno-transplantation (3). This encompasses the administration of human cells or tissue in usually immunodeficient animals. Excellent host animals for generating a human immune system are mouse lines that have several defects in the adaptive immunity such as $Rag2^{-/-}\gamma^{-/-}$ (4), BNX or NOD/SCID $B2m^{null}$. Different lines of the NOD/SCID (non-obese-diabetic/severe combined immunodeficiency) mouse serve as a standard model for humanization. They are characterized essentially by the following immunodeficiency properties: complete loss of B lymphocytes and T lymphocytes, reduced number of NK cells, defects in the differentiation and function of antigen-presenting cells and the absence of circulating complement. These mice are more susceptible for ionizing radiation than the wild type and have defects in the DNA repair system. The formation of human individual lines or several lines of hematopoiesis in an immunodeficient animal is possible after transplantation of human hematopoietic stem cells, differentiated hematopoietic cells as well as lymphoid organs. As a function of the utilized mouse line and its conditioning as well as the number and the source of hematopoietic stem cells, the development of 0.1 to 90% of human $OD45^+$ cells in peripheral blood or the spleen and bone marrow of animals is possible.

A disadvantage is the extremely high variability of the reconstitution of the hematopoiesis. Moreover, individual human cell types are represented differently, depending on the mouse line and the conditioning of the animals. Characteristic for the NOD/SCID mouse is that preferably and almost exclusively B cells will grow. The human B lymphocytes exhibit the typical pattern of immunoglobulin gene rearrangements (6) and generate a diverse immunoglobulin repertoire after administration of human fetal, umbilical cord blood or adult lymphoid progenitors (7). Circulating T-cells are absent or formed only in an extremely minimal amount and, moreover, are formed with delay. A fast and strong development of the T-lymphocytes is detectable only after pretreatment of the animals with recombinant tumor necrosis factor and the administration of high cell numbers of mononuclear cells (8). The human engraftment however has very high variances within the animal group. The phenotypification of the human T-cells shows, despite the variability, a CD4/CD8 quotient of 1:1 or 1:2 as a function of the employed stem cell source. The cells have a diverse T-cell receptor repertoire. Preliminary functional analyses of these T-cells show in in-vitro proliferation studies with PHA or IL-2 that they can be activated; however, only at a very low level. U.S. Pat. No. 6,627,792 B2 utilizes sections of rib bone tissue of operated patients that is applied subcutaneously into the peritoneal cavity for successful reconstitution of T-cells. Their availability and ethical concerns limit their use. After intravenous injection of individual cell suspensions of this bone tissue, the human chimerism is very low and T-cells could hardly be detected. U.S. Pat. No. 6,060,643 utilizes for reconstitution in BNX mice human hematopoietic cells of G-CSF mobilized peripheral blood (PB), fetal and adult bone marrow (FBM, ABM). Only 17% or 4.7% of the mice were chimeric after 6-8 weeks with an extremely high variability after transplantation of PB or ABM. No chimerism was obtained after administration of FSM. Less than 3% or 15% of the animals receiving transplants of PB or ABM or FBM demonstrated a long-term engraftment. Animals that received PB had an average survival rate of 25% after 30 days. This may be related to the fact that auto-reactive cells were formed or a regulatorily active cell population is not developed. Clear signs of a graft versus host disease were found only after administration of peripheral blood of adult donors (9). This demonstrates the unsatisfactory functional potency of human cells in the context of animal models up to now.

Up to now, human cells of the macrophage dendritic cell type have been detected only as immature $CD34^-$ $HLA\text{-}DR^+$ $CD4^+$ dendritic cell precursors (DC) after implantation of human mononuclear cells of the umbilical cord blood. No mature DCs could be detected in the lymphoid organs of the NOD/SCID mouse (10). Even though the differentiation of the DCs to the mature cells in the animal model was blocked, the DCs that matured under in-vitro conditions proved to be efficient stimulators in a mixed leucocyte reaction. Cravens et al. (11) demonstrated the development of human mature and reactive DOCs in the NOD/SCID mouse without additional cytokine addition. The cells react to an LPS stimulation in-vitro with a high cytokine secretion of IL-8, TNF-α. IL-10 as well as IL-12p70. Relatively low is the release of IL-1β, IL6 as well as IFNγ. These cytokines however are characteristic in the human system for an acute or systemic infection. Further developments are therefore required in which a cytokine profile that is comparable to the human system must be aimed at.

In summarizing the above, it is apparent that methods and models that exist currently reflect partially the development and maturing of human hematopoietic cells and their reactivity in an animal. However, currently there is no established method that generates a standardized, reproducible model that represents the totality of a human, in particulars adaptive, immune system. However, this is an absolute requirement in order to make testing in preclinical phases more efficient and to minimize therapeutic failure. The preparation as well as the use of human-specific therapeutic or regenerative agents requires a common functional presence of human dendritic cells, T-cells and B-cells, NK-cells, monocytes and granulocytes.

SUMMARY OF THE INVENTION

The problem to be solved by the invention is therefore to provide a new method for the permanent production of human-specific chimeras that does not have the disadvantages known from the prior art. In particular, it is an object of the invention to increase the reliability of growth of a transplant with cells that have a hematopoietic potential in animals and to minimize the inter-individual variability of the reconstitution result. In this way, the condition of homogenous experimental groups with comparative reaction patterns and strength is provided.

Moreover, it is an object of the invention to provide a permanent generation of all cells of the hematopoietic system in a balanced way as well as the development of cell-typical reaction patterns in an animal, respectively. The invention should enable the cooperation of human cells in their typical way in an animal and, in this way, provide a functional human, in particular, adaptive, immune system. The chimeras should show no, or only minimal signs, of a transplant-caused reaction against the host organism. In addition, the method-based partially very high mortality of the animals (15-65%) should be minimized.

As a solution to this object, the invention provides a method that by means of a new conditioning method of the host animals overcomes the prior art disadvantages of the known solutions.

According to the invention, the object is solved by a method for producing an animal model for the human immune system in a non-human mammal with the steps of:
 a) transplantation of human stem cells with hematopoietic potential into the non-human mammal; and
 b) conditioning the non-human mammal with cell culture supernatant of a culture of human cell lines, cells and/or tissue, and optionally,
 c) administration of support cells having no hematopoietic potential of their own.

The invention is characterized by the utilization of "conditioned cell culture supernatants" that contain combinations (cocktails) of messenger substances, particularly of human origin. In connection with the administration of human stem cells, they are used for producing the inventive animal model (immune system chimeras) in preferably immunodeficient animals.

The method according to the invention enables advantageously the formation of B-lymphocytes and T-lymphocytes, NK cells, monocytes, granulocytes, hematopoietic stem cells as well as dendritic cells and the development of cell type-specific reactions of these cells. Accordingly, a model is made available which reflects the human, in particular, adaptive, immune system with respect to significant characteristics of its functionality. The method is useful for all in-vivo or derived in-vitro applications in which immunological processes with human cells are required for diagnostic purposes, for research purposes, for the development and testing of medical therapies or for the development of products. Examples are the production and use of monoclonal human antibodies, development of vaccination strategies, animal-experimental disease models, testing of pharmacological active ingredients, development of strategies for induction of immune tolerance after organ transplantation in particular by employing human, humanized or murine antibodies.

The important features according to the invention of the method represented in the claims as well as the claims presented in the additional claims will be explained in the following in generalized form.

Considered important for the invention for generating a chimera is the conditioning with "conditioned cell culture supernatant" used alone or in combination with support cells.

The "conditioned cell culture supernatant" is defined as a cell-free, soluble phase that has been separated from cells present individually or in a tissue sample after different molecules have been secreted into the cell culture supernatant during an incubation phase. Moreover, cell-free body liquids, for example, plasma, serum, or ascites are also encompassed by this term. The secreting cells should preferably belong to the same species as the stem cell source that is utilized for generating a chimera. Preferably, human cell lines that produce permanently or after suitable stimulation or differentiation soluble factors such as cytokines should be used for producing the cell culture supernatant. Examples are the cell lines 358/8 (derived from NCI-H358, European Collection of Cell Cultures, Salisbury, Wiltshire, UK, No. 95111733) and subclones derived therefrom (subclone SC25, obtained from Institut für Zoologie: Universität Leipzig), A-549 (human type II pneumocytes, LGC Promochem, Cell Biology Collection ATCC® No. CCL-185™, London UK) as well as VA-ES-BJ (human epitheloid sarcoma cell line, Deutsche Sammlung für Mikroorganismem und Zellkulturen GmbH, Braunschweig, DE, ACO 328).

The cell culture supernatant contains preferably the factors that are contained in a cell culture supernatant of a cell line selected from 35818. A-549, and VA-ES-BJ, or in a mixed cell culture supernatant of two or three of the aforementioned cell lines.

It was found to be advantageous when in the cell culture supernatant the factors IL-8, IL-6, VEGF, IP-10, MCP-1, ANG and t-PA are present.

IL-8, IL-6, VEGF, IP-10, MCP-1, ANG and t-PA are present in the aforementioned cell culture supernatants preferably in concentration ranges of, respectively, 20 pg/ml to 10 ng/ml.

It is especially preferred that the cytokines are contained in the aforementioned culture supernatants in the concentration ranges listed in the following: IL-8 (500 pg/ml to 10 ng/ml), IL-6 (50 pg/ml to 10 ng/ml), VEGF (500 pg/ml to 10 ng/ml), IP-10 (20 pg/ml to 1 ng/ml), MOP-1 (500 pg/ml to 10 ng/ml), ANG (20 pg/ml to 1 ng/ml), und tPA (500 pg/ml to 15 ng/ml).

In contrast, the presence of TNF-α, IL-10, MIG, RANTES, sVCAM-1, sCD40L, bFGF, sP selectin or IgF is not required or not required in high concentrations (≤20 pg/ml).

The point in time of this conditioning with cell culture supernatant can be before as well as after the transplantation day on one day or over several days. The administration quantity should not be contrary to the general recommendations that are anchored in the guidelines for the treatment of test animals.

The conditioned culture supernatant is preferably administered directly after cellular transplantation and subsequently administered every other day for a time period of 14 days.

There is no limitation as regards the administration location. However, recommended is an intravenous or intraperitoneal administration. In the case of mice, an intraperitoneal administration with an amount of approximately 200 µl, preferably 150 µl to 250 µl per administration, is the goal. It is expedient to test the compatibility of each selected "conditioned cell culture supernatant," in the animal model before transplantation.

In addition to the administration of the stem cell-containing source, in a special variant of the method according to the invention so-called "support cells" that have no hematopoietic potential on their own are applied. In this connection, for example, stem cell-depleted (maximal stem cell contents ≤0.1%) or stem cell-negative cell populations (maximal stem cell contents ≤0.01%)) of a stem cells source as well as mesenchymal stem cells can be used. The use of "support cells" with oncogenic potential should be avoided. For example, CD34-negative or CD133-negative mononuclear cells of the umbilical cord blood or the bone marrow should be used as support cells. The support cells are used preferably in concentration ranges of $1\times10^4$ to $5\times10^7$ cells per cell transplant. The administration of the support cells is realized preferably together with the stem cell-containing population.

Preferred for the animal model is the utilization of immunodeficient mammals, preferably rodents, particularly preferred mice, that serve as host animals for creating chimerism. The gender of the animals is not important. In particular mice should have an age of more than six weeks. The method is facilitated when the recipient is the offspring of an incest line that has several immune defects primarily in the adaptive immune response. Preferred are mouse lines SCID as well as NOD/SCID (Jackson Laboratory, Bar Harbor, Me., USA), $Rag2^{-/-}\gamma^{-/-}$ (Taconic Animal Models, Lille Skensved, DK), BNX (Taconic Animal Models, Lille Skensved, DK) or NOD/SCID B2m$^{null}$ (Jackson Laboratory, Bar Harbor, Me., USA), NOD/SCID IL-2-receptor-γ-chain$^{null}$ (Jackson Laboratory, Bar Harbor, Me. USA). Primarily immunodeficient animals should be kept under specific pathogen-free conditions; otherwise, standard keeping is sufficient.

The stem cells required for generating the chimerism can be taken from any stem cell containing source. Preferably, these cells should have a hematopoietic (blood-generating) potential. Such hematopoietic stem cells are cells that can proliferate and are able to generate all cells of the hematopoietic system, in particular, the immune system. Such stem cells can be found primarily in preparations of human bone marrow, mobilized as well as non-mobilized peripheral blood, umbilical cord blood and umbilical cord tissue. The stem cells employed in accordance with the invention are able to generate cells of the human immune system. In particular, the stem cells can differentiate into B-lymphocytes and T-lymphocytes, NK cells, monocytes, granulocytes, as well as dendritic cells.

The age and gender of the donor are not important. Enrichment of the stem cells is possible but generally not required. Preferably, a mononuclear individual cell fraction should be made available. The removal of erythrocytes as well as granulocytes by conventional methods is recommended. Freshly obtained as well as kryogenically preserved preparations can be utilized. Cell dyeing with selected vital dyes such as CFSE does not impair the success of the method.

In general, animals in which chimerism is to be generated, are made more receptive by conditioning that inter alia is aimed at removal of residual animal immune-competent cells for a subsequent transplantation of the stem cells. Preferably, this is done by radioactive irradiation of the recipient organism. As a radiation source radioactive isotopes as well as x-ray devices can be utilized. The irradiation should not surpass the recommended animal-specific sublethal dose. This dose is individually determined for each breed line. In general, a one time irradiation and not multiple irradiations should be carried out. The sublethal dose for a single irradiation for NOD/SCID mice is in general 250-350 cGy.

The administration of the transplant can be done shortly after conditioning by irradiation or with delay. The term shortly after implies administration immediately after the irradiation, while a delay encompasses several days. In general, a temporal window of 3 to 24 hours after irradiation is taken into consideration. The administration location of the transplant is not mandatorily prescribed. For individual cell suspensions an intravenous or intraperitoneal administration is preferred. The animals, as needed, can be anesthetized. Preferably, $1\times10^3$ to $5\times10^7$ mononuclear cells that contain the stem cells are transplanted per mouse. The contents of CD34-positive stem cells is preferably in a range of 5 to $5\times10^5$, preferably $1\times10^3$ to $1\times10^4$.

After transplantation, the animals are kept under standard conditions or specific pathogen-free conditions.

The development of the generated chimerism is determined by controls, at regular intervals, based on samples of the peripheral blood of the transplant-recipient animal. In mice, especially harvesting blood from the retrobulbar ocular plexus or from the tail vein is expedient. The proportion of human cells is determined preferably by means of flow-cytometric examinations by employing human-specific antibodies (line markers, differentiation antigens, activation markers). In case of a minimal sample volume, it is recommended to employing, respectively, a species-specific pan-leucocyte marker such as CD45, if possible in a direct comparison of donor and recipients species.

Advantageously, when applying the method according to the invention, already 14 days after transplantation a safe detection of human cells in the periphery is possible. This form of monitoring enables under the conditions of the invention a reliable conclusion in regard to the temporal reconstitution success. Moreover, the presence of human cells in the periphery correlates with an engraftment in the spleen and bone marrow.

The present invention overcomes the problems and disadvantages of the prior art for producing the human-chimeric animals in that a new standardizable, highly reproducible method by employing a new conditioning method of the animals is provided in connection with human stem cells.

The method enables the provision of chimeras of equal value and provides thus a reduction of the high interindividual variability known in the prior art. Under the conditions of the invention a mortality rate of only 10% is observed.

A new aspect according to the invention is the reliable realization of chimeras that form human immune-competent cells of the hematopoietic system.

A further object of the invention is therefore an animal model for the human immune system in a non-human mammal which contains human immune-competent cells of the hematopoietic system. Encompassed are in particular T-cells and B-cells, monocytes, dendritic cells, NK cells, granulocytes, as well as CD34 stem cells. All animals exhibit under the conditions of the invention a human engraftment in the peripheral blood, the spleen, and the bone marrow.

Advantageous is the permanent reconstitution of the hematopoiesis. The expression as well as composition of the human hemogram that were assayed on day 56 after transplantation in a NOD/SCID mouse treated according to the invention were detectable advantageously for a time period of 5 months. The animal model produced according to the present invention for the human immune system is therefore very stable.

The invention advantageously provides animals that express an immune system that is comparable (equivalent) to that of humans with special focus on a reactive adaptive immune system. In the animal model according to the invention the human immune competent cells advantageously have a comparable functionality as in the human body, in particular a comparable response to antigens and cytokine profile that is comparable to the human profile.

The human dendritic cells in the animal model are capable of producing human interleukin-8 constitutively and of producing human interleukin-6, human interleukin-1β, and human tumor necrosis factor-α (TNF-α) after immune stimulation (for example, with LPS).

Surprisingly, the animals show no visible signs of a graft versus host disease. As a result of the new stable expression of human hematopoietic stem cells in the recipient organism, a further transplantation of cells that are derived therefrom can be advantageously carried out in one or several secondary recipients and, in this way, a further multiplication of chimeric organisms can be performed.

The conditioned transplant-recipient animals have in their spleen within the range of human cells a balanced quantity of T-cells (median; 29%) and B-cells (median: 20%). Moreover, human NK cells (median: 0.36%), monocytes (median: 1.1%), granulocytes (median: 4%) as well as CD34-positive stem cells (median: 0.7%) can be detected. The median is based on examinations of 21 animals.

The formation of human immunoglobulin M as well as immunoglobulin G in vivo as evidence of the activity of the human B-cells was proven.

The high reactivity of dendritic cells (0.2%-2.4% of the human cells in the bone marrow) was demonstrated by cytokine production after LPS stimulation in-vitro. The cells produce 24 hours as well as 48 hours after stimulation cytokines such as IL-1β (more than 1,000 pg/ml), IL-6 (more than 5,000 pg/ml), TNF-α (more than 90 pg/ml) as well as IL-10 (more than 100 pg/ml). Cytokine IL-8 is secreted already constitutively. This cytokine pattern is comparable to an infectious event in the human. With the reactivity of the dendritic cells as potent antigen-presenting cells (exogenic as well as endogenic antigens) that have a key role in the activation and expression of an adaptive immune response and the simultaneous presence of reactive human T-cells as well as B-cells, a functionality of the (chimeric) animal model is provided that is equivalent to the human immune system.

The functionality of the human adaptive immune system in the mouse has been demonstrated unequivocally by confirming an induced T-cell-dependent antigen-specific antibody production (immunization). Maturing of the immune response in the form of generating antigen-specific antibodies of the immunoglobulin G isotype has been proven.

The animal model according to the invention thus represents advantageously a model system for the human immune system that is suitable for product development and research, in particular, pharmacological research, preclinical studies, pathogenesis research, development of new diagnostic strategies or therapeutic strategies.

The present method for producing human reactive chimeras and the animal model produced thereby in accordance with the invention enables advantageously the production of human monoclonal as well as polyclonal antibodies. Particularly important is the production of complete human antibodies without animal-based foreign proportion and complete physiological gycolization. These human antibodies are very important on the pharmaceutical market, therapeutics market as well as diagnostics market.

The human cells generated in accordance with the invention in the animal model have advantageously the capability of detecting exogenic as well as endogenic antigens and to produce based thereon an immune response. Based on this, inter alia, possibilities can be derived for producing antigen-specific dendritic cells, testing immune therapeutic protocols, for example, by employing human, humanized or murine therapeutic antibodies, characterizing immune-modulatory substances (chromatin modifiers, "small molecules") or immune-modulatory effective cell populations (mesenchymal stem cells, regulatory T-cells, tissue engineered products).

This model can advantageously be utilized as a platform technology for the further development of models for infectious diseases (such as HSV, EBV, HIV, rubella), autoimmune diseases, tumorous diseases, transplantation-associated diseases or inflammatory diseases and therapeutic strategies.

BRIEF DESCRIPTION OF THE DRAWINGS

In the following, the method according to the invention will be explained with the aid of one embodiment and the correlated Figures.

FIGS. 1a and 1b show the results of a flow cytometric analysis of peripheral blood, spleen, and bone marrow 8 weeks after transplantation of transplant-recipient NOD/SCID animals with administration of conditioned supernatant.

FIG. 3a shows the control without and FIG. 3b with administration of the conditioned supernatant.

DESCRIPTION OF PREFERRED EMBODIMENTS

1. Preparation of the Conditioned Supernatant

Figure 1B:
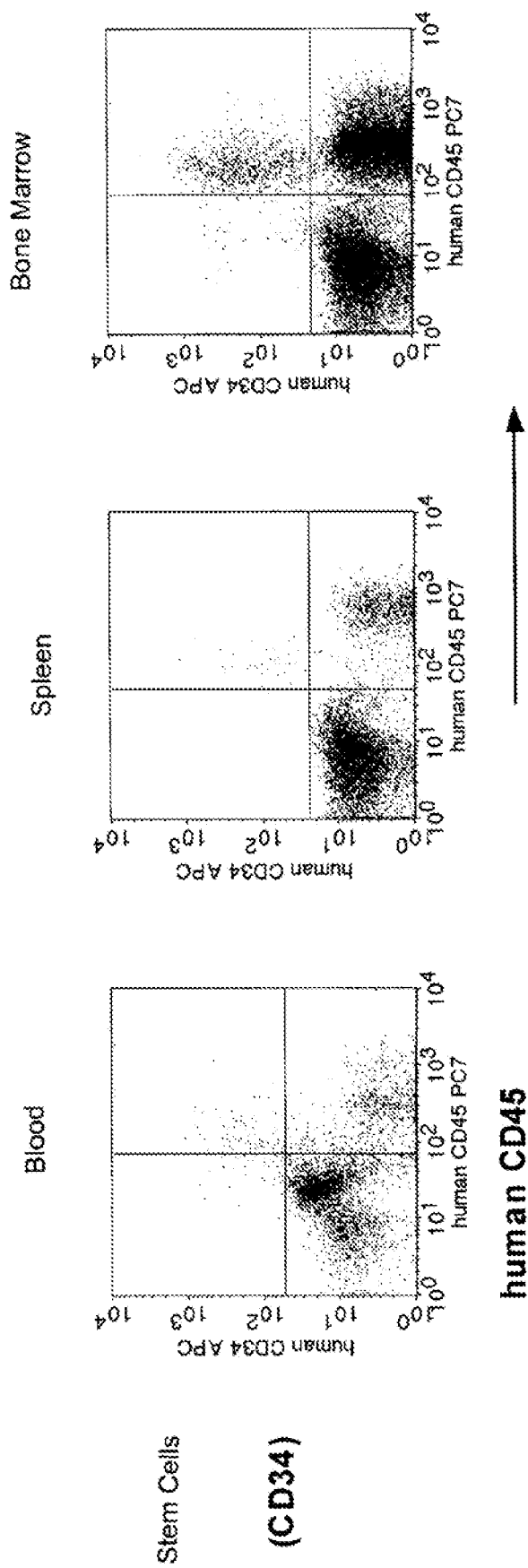

A human lung cell carcinoma cell line (here type II pneumocyte line 358/8 subclone [derived from NCI-H358] obtained from Institut für Zoologie, Universität Leipzig) or, alternatively, the sarcoma cell line (VA-ES-BL, Deutsche Sammlung für Mikroorganismen und Zellkulturen GmbH, Braunschweig, DE, ACC 328) is grown under sterile conditions in RPMI 1640 with addition of 5% fetal calf serum until it has reached the logarithmic growth phase. For producing the conditioned medium $2-4 \times 10^5$ cells/ml were seeded. The culture medium is harvested after 3 days, collected, filtered under sterile conditions (pore size 0.2 µm) and stored in portions at least −20 EC until further use.

In the conditioned culture supernatant the cytokines are contained in the subsequently listed concentration ranges, IL-8 (500 pg/ml to 10 ng/ml) IL-6 (50 pg/ml to 1 ng/ml), VEGF (500 pg/ml to 10 ng/ml), IP-10 (20 pg/ml to 1 ng/ml), MCP-1 (500 pg/ml to 10 ng/ml), ANG (20 pg/ml to 1 ng/ml), and tPA (500 pg/ml to 15 ng/ml).

The presence of TNF-α IL-10 MIG, RANTES, sVCAM-1, sCD40L, bFGF, sP-selectin or IGF is however not detectable or not detectable at higher concentrations (≤20 pg/ml).

2. Method for Generating the Human Immune System in Mice

Male as well as female NOD/SCID mice (Jackson Laboratories, USA) of at least six weeks of age were kept under specific pathogen-free conditions and served as recipients. The whole body irradiation of the animals was carried out at 350 cGy by means of an x-ray therapy device, 3-5 hours after irradiation, $1-10 \times 10^6$ mononuclear cells, isolated from human umbilical cord blood, were administered into the tail vein of an ether-anaesthetized animal. Cells derived from individual blood of a donor as well as cells of several mixed blood samples were utilized. The mononuclear cells were isolated by means of density gradient centrifugation by using lymphocyte separating medium LSM 1077 (PAA Laboratories, Pasching, AT) according to the method of Boyum (1976). The mononuclear cell fraction was stored before transplantation for at least 24 hours at −196 EC and at the day of transplantation was thawed in time. Until transplantation was carried out, the cells were stored in a medium or PBS at 4 EC. After administration of the cells, immediately the first dose of 200 µl of the conditioned cell culture supernatant of the human pneumocyte cell line obtained as described above was administered intraperitoneally. Further doses of the supernatant were administered every two days until day 14 after transplantation without sedation of the animal.

In order to demonstrate the effect of the additional conditioning, comparative groups received the respective cell fractions without administration of the cell culture supernatant.

3. Characterization of the Human Chimerism as Well as the Functionality of the Immune System As a control of the human hematopoietic reconstitution of the mice, every 2 weeks, beginning at day 14 after transplantation, blood samples of approximately 75 µl were taken from each mouse by punctuation of the tail vein or slight scoring of the tail vein by means of a scalpel. For preventing coagulation, sodium heparin was added to the samples and subsequently, the samples were mixed well. 8 weeks after transplantation, the mice were killed for determining the human long-term engraftment and the peripheral blood, the spleen, the bone-marrow as well as the liver of the animal were isolated. Individual cell suspensions were produced mechanically from the solid organs. As needed, filtration through a nylon filter for separation of connective tissue of the cells was carried out. Erythrocytes were lysed either with distilled water or by means of ammonium chloride-containing buffer. For characterizing the engraftment, directly conjugated human-specific antibodies were used that had been tested before analysis with regard to possible cross reactivity with murine antigens. The following human-specific antibodies were utilized: CD45, CD3, CD19, CD56, CD14, CD16, CD34, HLA-DR, anti-lineage cocktail, OD11c, CD123 (Becton Dickinson, Heidelberg, DE). Moreover, for the purpose of specificity control, marking with a murine-specific CD45 antibody (IQ Products, Oldenburg, DE) was carried out. The data in regard to the individual lines is based on the relative proportion of human CD45 positive cells. The marked samples were analyzed by means of a FACS Calibur (Becton Dickinson). Recipients exhibited a human chimerism when they had a contents of human CD45-positive cells of ≤0.1%.

After transplantation of $5 \times 10^6$ as well as $10 \times 10^6$ of mononuclear cells of the umbilical cord blood by utilizing conditioned cell culture supernatant all animals shows human chimerism. The mortality of the animals was at 10%.

FIGS. 1a and 1b show the results of a flow cytometric analysis of peripheral blood, spleen, and bone marrow 8 weeks after transplantation of transplant-recipient NOD/SCID animals with administration of conditioned supernatant. The dot plots show living cells characterized by human-specific antibodies such as CD19 (general B-cell marker) in FIG. 1a (top row), CD3 (general T-cell marker) in FIG. 1a (bottom row), CD34 (stem cell marker, comprises primarily hematopoietic stem cells as well as line-imprinted precursor cells) in FIG. 1b plotted against CD45 (general lycocyte marker), respectively.

As shown in FIGS. 1a and 1b, human T-lymphocytes as well as human B-lymphocytes and human hematopoietic stem cells were generated. Moreover, human monocytes as well as human NK cells as well as human granulocytes were detected. The aforementioned cell populations can be detected in all hematopoietic organs such as peripheral blood, spleen, and bone-marrow.

Figure 2A:
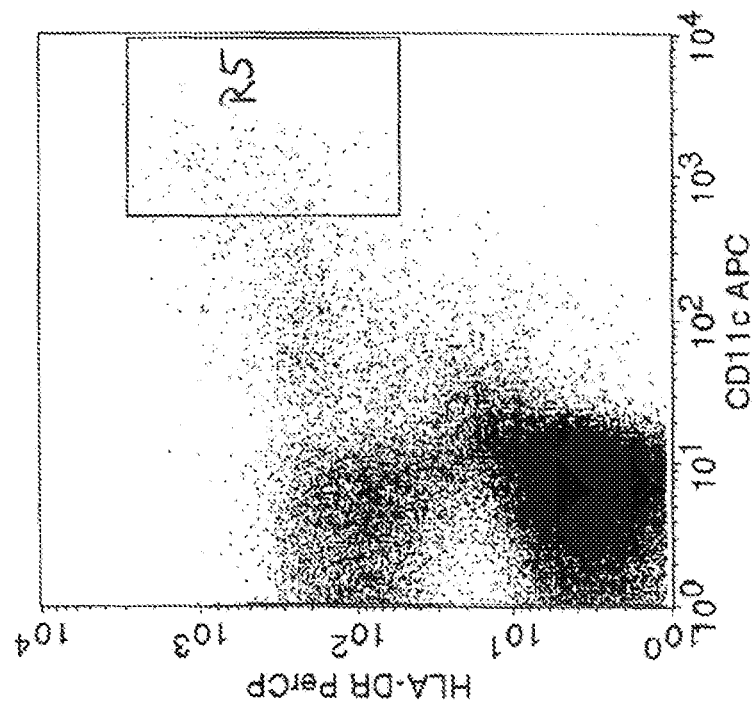
FIG. 2a shows a flow cytometric analysis of bone marrow (representative of spleen and peripheral blood) 8 weeks after transplantation in transplant-recipient NOD/SCID animals with administration of the conditioned supernatant.

FIG. 2a shows a flow cytometric analysis of bone marrow (representative of spleen and peripheral blood) 8 weeks after transplantation in transplant-recipient NOD/SCID animals with administration of the conditioned supernatant. The dot plots show human dendritic cells characterized by the expression of human-specific antigens such as HLA-DR, CD11c (right blot, region R5) or CD123 (left blot, region R4) as well as the absence of line-typical antigens such as CD3 (general T-cell marker), CD16 (marker of neutrophilic granulocytes, subpopulation of NK cells, and monocytes, macrophages), CD19 and CD20 (general B-cell marker), CD14 (monocyte marker, detection of macrophages, neutrophils, eosinophils) as well as CD56 (general NK cell marker, subpopulation of T-cells) contained in an anti-lineage cocktail antibody mixture.

In FIG. 2a living cells are illustrated that have no or only minimal expression of line-typical antigens. These cells contain two human dendritic cell populations.

The plasmoidic dendritic cell population is characterized by the expression of CD123 as well as HLA-DR (FIG. 2a, left blot, region R4). In the bone marrow of chimeric animals a median of 0.21% of the cells are plasmoidic dendritic cells. After a systemic administration of LPS (10 μg/mouse), as an analogon of a systemic bacterial infection, the proportion of the plasmoidic dendritic cells increases to 2.4%.

The myeloid dendritic cell population expresses on the cell surface CD11c as well as HLA-DR (FIG. 2a, right blot, region R5). In the bone marrow of the chimeric animals a median of 0.17% of the cells are myeloid dendritic cells. After a systemic administration of LPS (10 μg/mouse), as an analogon of a systemic bacterial infection, the proportion of the myeloid dendritic cells increases to 2.1%.

Dendritic cells are an important representative of the antigen-presenting cells and form the basis for producing an adaptive immune response. Moreover, they are involved significantly in the process of developing immune tolerance. The functional reactivity of the cells is derived from the increase of the proportion of the dendritic cells after a systemic stimulation with LPS.

Moreover human basophil cells (effector cells of allergic type I reactions) were detected (FIG. 2a, left blot, region R3).

Figure 2A:
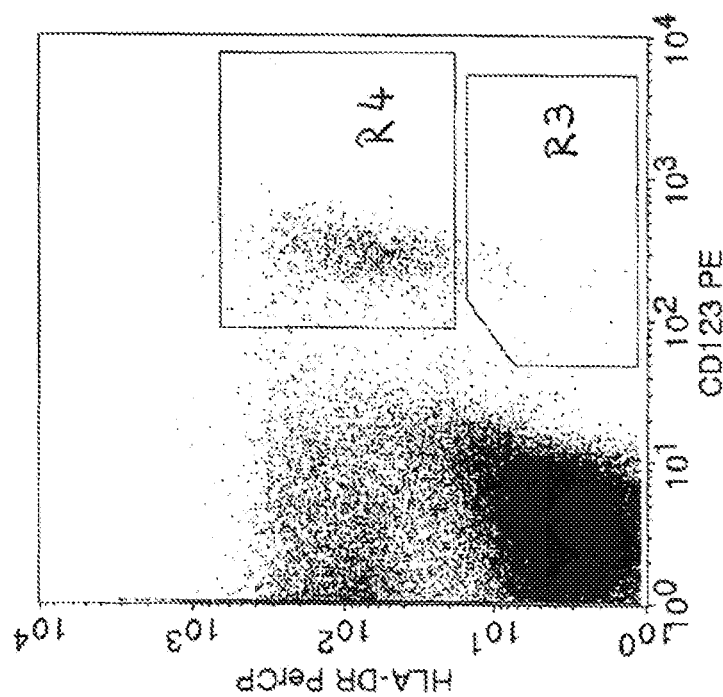
Figure 2B:
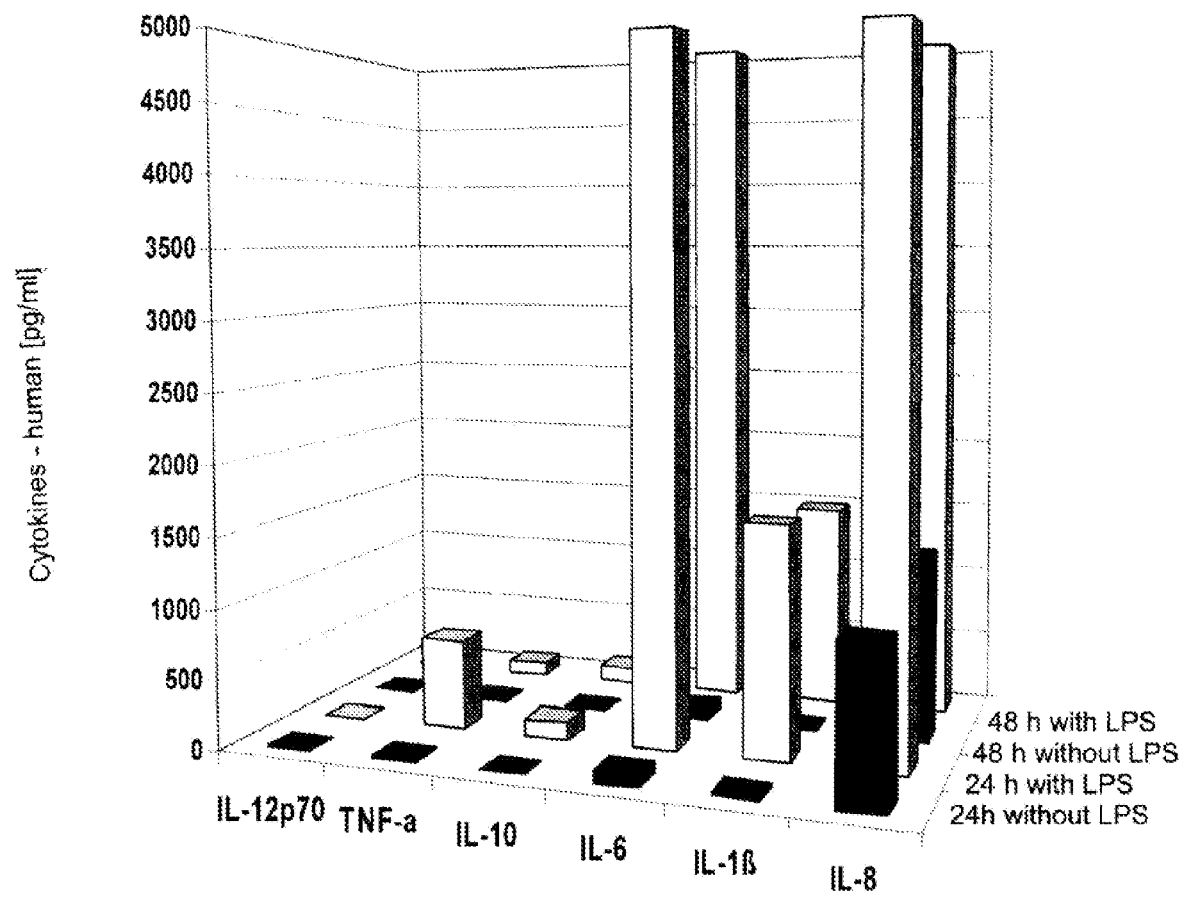
FIG. 2b shows a comparison of the cytokine release of isolated bone marrow cells after LPS stimulation (10 g/ml, white bar) of humanized NOD/SCID mice with administration of conditioned supernatant relative to a control without stimulation (black bar).

FIG. 2b compares the cytokine release of isolated bone marrow cells after LPS stimulation (10 μg/ml, white bar) of humanized NOD/SCID mice with administration of conditioned supernatant relative to a control without stimulation (black bar).

For testing the activity of the human cells, bone marrow cells of a reconstituted NOD/SCID mouse were stimulated in vitro with LPS as an analogon to an infection. Controls without stimulation were performed as well. 24 hours and 48 hours after stimulation, the determination of human-specific cytokines such as IL-1β, IL-6, IL-8, IL-10, IL-12p70 as well as TNF-α in the culture supernatant by means of RD cytometric bead array analysis was carried out on FACS-Scan (Becton Dickinson).

Based on a strong inducible cytokine release the reactivity of the human dendritic cells was demonstrated clearly (FIG. 2b). The cells produce 24 hours as well as 48 hours after stimulation cytokines such as IL-1β (more than 1,000 pg/ml), IL-6 (more than 5,000 pg/ml), TNF-α (more than 90 pg/ml) as well as IL-10 (more than 100 pg/ml). The cytokine IL-8 is secreted already constitutively. The cytokine pattern is comparable to a cytokine pattern of an infectious event in humans. Moreover, on the basis of the absence of, or the minimal, cytokine secretion of IL-1β, IL-6, IL-10, TNF-α as well as IL-12p70 in the control cultures, it can be stated that the cells of the bone marrow do not exhibit a pre-stimulation indicating an inflammatory event in the reconstituted mouse.

Figure 3A:
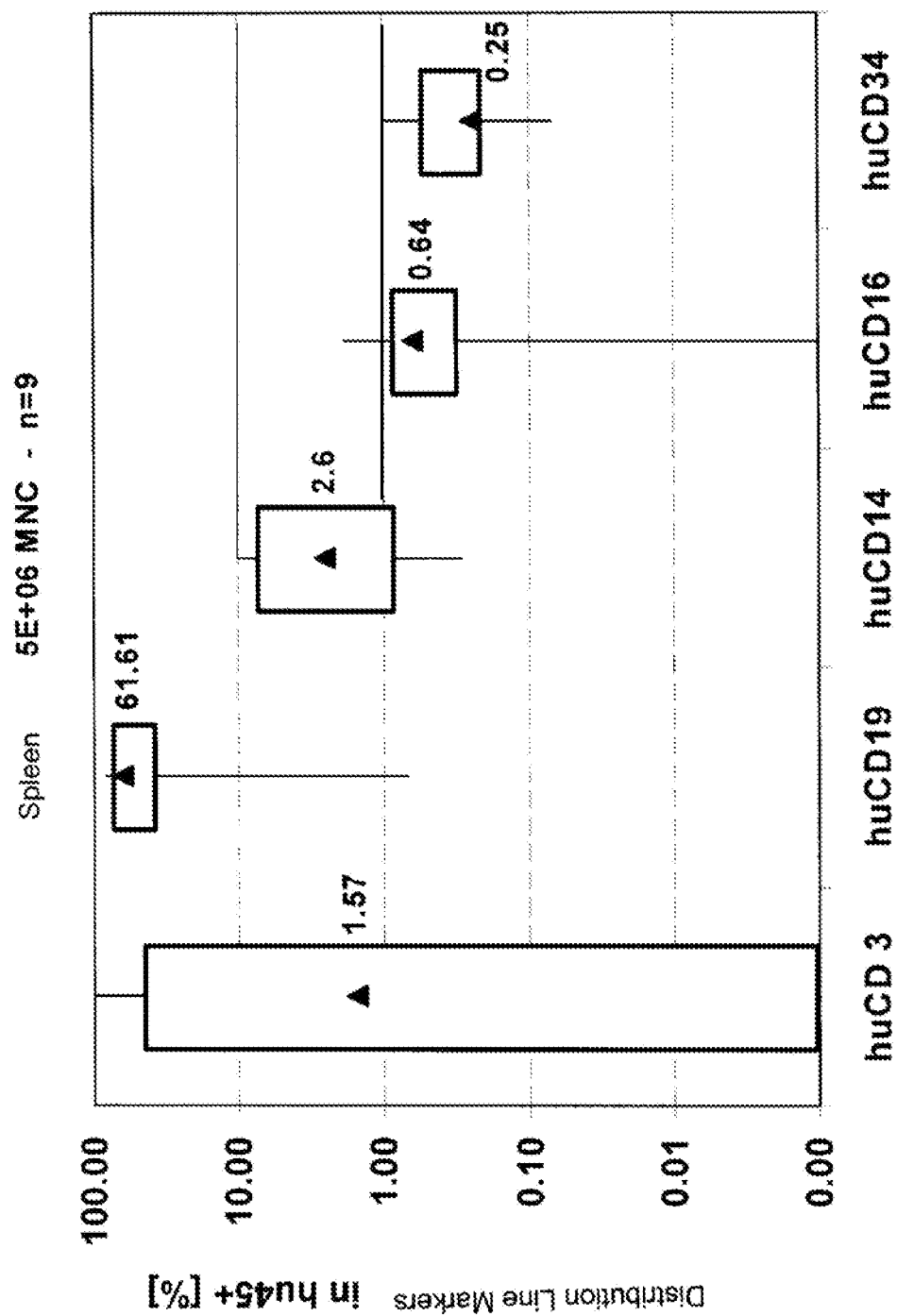
FIGS. 3a and 3b show the effect of administration of the conditioned cell culture supernatant on the distribution of human T-lymphocytes and B-lymphocytes in the spleen of transplant-recipient mice.
Figure 3B:
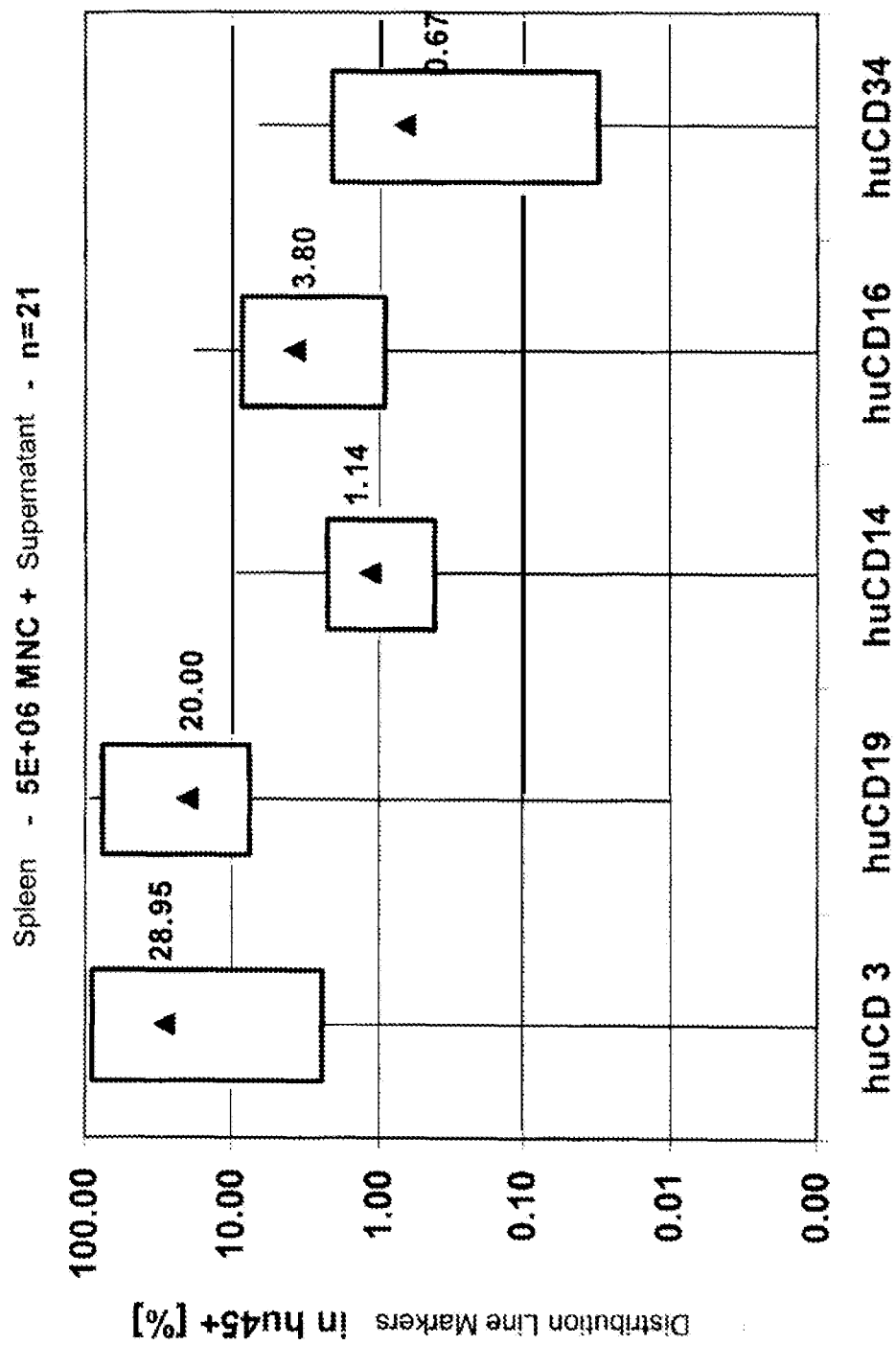

FIGS. 3a and 3b show the effect of administration of the conditioned cell culture supernatant on the distribution of human T-lymphocytes and B-lymphocytes in the spleen of transplant-recipient mice. FIG. 3a shows the control without and FIG. 3b with administration of the conditioned supernatant. The data relating to the individual cell lines (median, black triangles, and numbers to the right adjacent to the bars) is provided as a relative proportion of human CD45-positive cells. The bars represent the distribution (2 quartiles as well as the two extreme values) within the test animals.

As a comparison to the control, the effect of conditioning on the distribution of the T-lymphocytes as well as B-lymphocytes is illustrated in FIG. 3. Without administration of the conditioned cell culture supernatant (FIG. 3a) the humanized animals produce predominantly B-cells (median: 62% CD19-positive cells) that can be detected in the blood as well as in the spleen and in the bone marrow. The animals have a median of only 1.6% T-cells (CD3-positive cells).

On the other hand, after administration of the conditioned cell culture supernatant (FIG. 3b), balanced quantities of T-cells (29% CD3-positive cells) as well as B-cells (20% CD19-positive cells) are formed. These animals have a median distribution of 1% monocytes/macrophages (CD14-positive cells), 4% CD16-positive cells (NK cells, granulocytes, subpopulation of monocytes) as well as 0.7% CD34-positive stem cells or imprinted precursor cells. Based on the balanced distribution of B-lymphocytes and T-lymphocytes, the prerequisite is provided to generate specific immune reactions, in particular, T-cell dependent immune reaction. All chimeric animals produced, after administration of the conditioned cell culture supernatant, a CD34-positive stem cell population localized in particular in the bone marrow. In this way, a permanent hematopoiesis is ensured in the animals. Accordingly, by means of a transplantation of the bone marrow of selected chimeric animals into further recipients, a multiplication under selective conditions can be carried out.

With the detection of the individual human cell types (FIGS. 1, 2, 3), the prerequisites for the functional reactivity particularly of an adaptive immune system are provided.

Figure 4A:
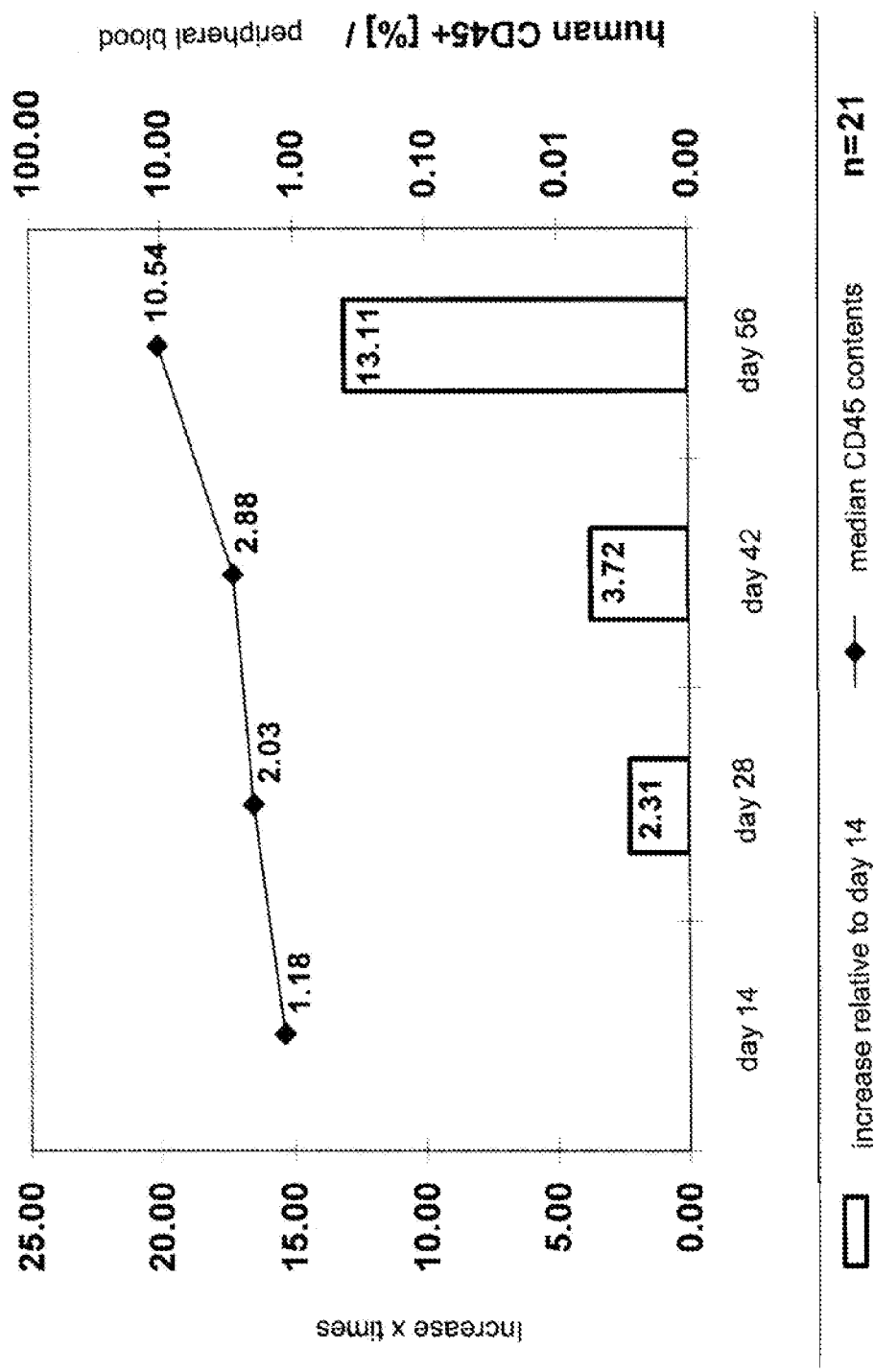
FIGS. 4a and 4b show the kinetics of the generation of a human chimerism after transplantation of human mononuclear cells by utilization of the conditioned supernatant. Recipients that have a contents of human CD45-positive cells of 0.1% of all cells exhibit human chimerism.
Figure 4B:
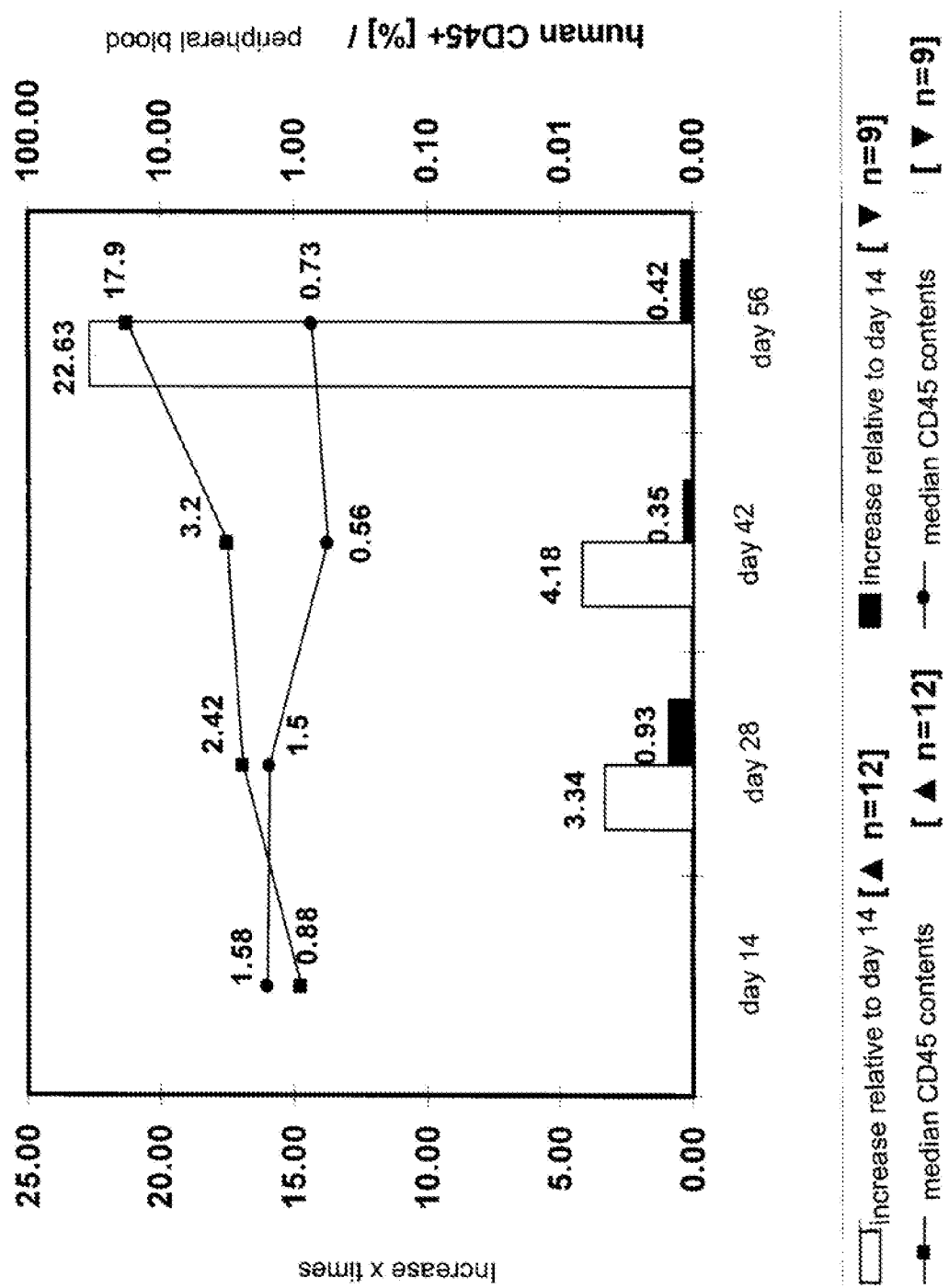

FIGS. 4a and 4b show the kinetics of the generation of a human chimerism after transplantation of human mononuclear cells by utilization of the conditioned supernatant. Recipients that have a contents of human CD45-positive cells of ≥0.1% of all cells exhibit human chimerism.

In this connection, FIG. 4a shows the median contents of human CD45-positive cells in the blood of all animals into which $5 \times 10^6$ MNC have been transplanted (black line with diamonds) as well as the increase of the contents of human CD45-positive cells relative to day 14 (white bars).

FIG. 4b shows the average contents of human CD45-positive cells in the blood of animals into which $5 \times 10^6$ MNC have been transplanted as a function of the development of the human engraftment. Grouping of the animals was based on "low" responders (increase of the relative proportion of CD45-positive cells <1 relative to day 14, n=9 [9 animals]) as well as "high" responders (increase of the relative proportion CD45-positive cells >1 relative to day 14, n=12 [12 animals]).

The data for the "low": responders (triangles with tip pointing down) are represented by the black line with circles and the black bars. The data for the "high" responders (triangles with tip pointing upwardly) are represented by the black line with squares and the white bars. The surface molecule CD45 is expressed by all leucocytes. Accordingly, the contents of human CD45-positive cells represents the development of the human hematopoietic system in the host.

All animals showed after administration of $5 \times 10^6$ cells a human engraftment that is detectable at any point in time (contents of human CD45-positives cells ≥0.1% of all cells). As illustrated in FIG. 4a, the proportion of CD45-positive cells in the blood increases continuously from day 14 after transplantation to day 56. On day 56 on average a 13 time increase can be detected. The average contents of human CD45-positive cells in the blood of all transplanted animals is 10.5%. However, within the test animal group a subdivision in good and bad responders can be found that can be determined already early on by means of the determination of the CD45 cell contents. The subdivision was realized by determination of the increase of the contents of human CD45-positive cells in the blood on all further analysis days relative to day 14. A value greater than 1 defines "high" responders, a value smaller than 1 "low" responders. Accordingly, already on day 28, with great reliability on day 42, after transplantation a clear statement in regard to the reconstitution capability of the individual animals can be made (FIG. 4b). "High" responders have on day 56 after transplantation on average 18% human CD45-positive cells in the blood while "low" responders have on average only 0.7%.

Figure 5:
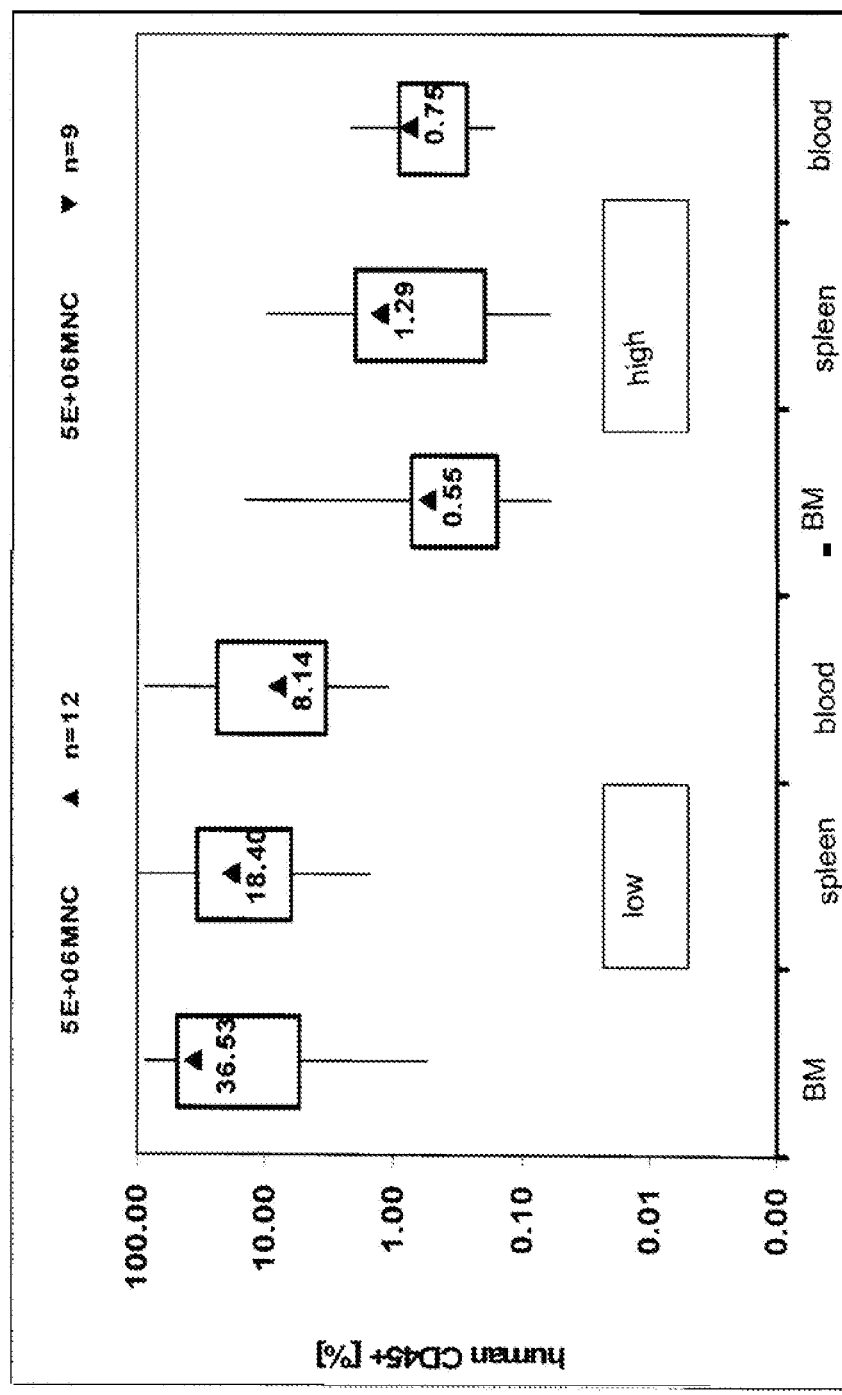
FIG. 5 shows an illustration of the median relative contents of human CD45-positive cells in lymphatic organs (day 56 after transplantation) of humanized mice after administration of the conditioned supernatant as a function of a low and high engraftment.

FIG. 5 shows an illustration of the median relative contents of human CD45-positive cells in lymphatic organs (day 56 after transplantation) of humanized mice after administration of the conditioned supernatant as a function of a low and high engraftment. Grouping of the animals is realized as described in connection with FIG. 4b in "high" responders (left side of FIG. 5—"high", n=12 [12 animals]) and "low" responders (right side of FIG. 5—"low", n=9 [9 animals]).

The determination of the relative contents of human CD45-positive cells in the peripheral blood correlates to a high degree with the contents of the human cells in the spleen as well as in the bone marrow (BM) (FIG. 5). Accordingly, "high" responders have a median (black triangles in FIG. 5) of 36.5% of human CD45-positive cells in the bone marrow and "low" responders, on the other hand, have only 0.6%. Comparative conditions are reflected in the distribution of cells in the spleen (18.4% versus 1.3%).

Accordingly, the determination of the increase of the contents of human CD45-positive cells in peripheral blood allows early selection of test animal groups with low inter-individual deviations for further experiments. The illustrated results demonstrate also that all hematopoietic organs are colonized with human cells.

Figure 6:
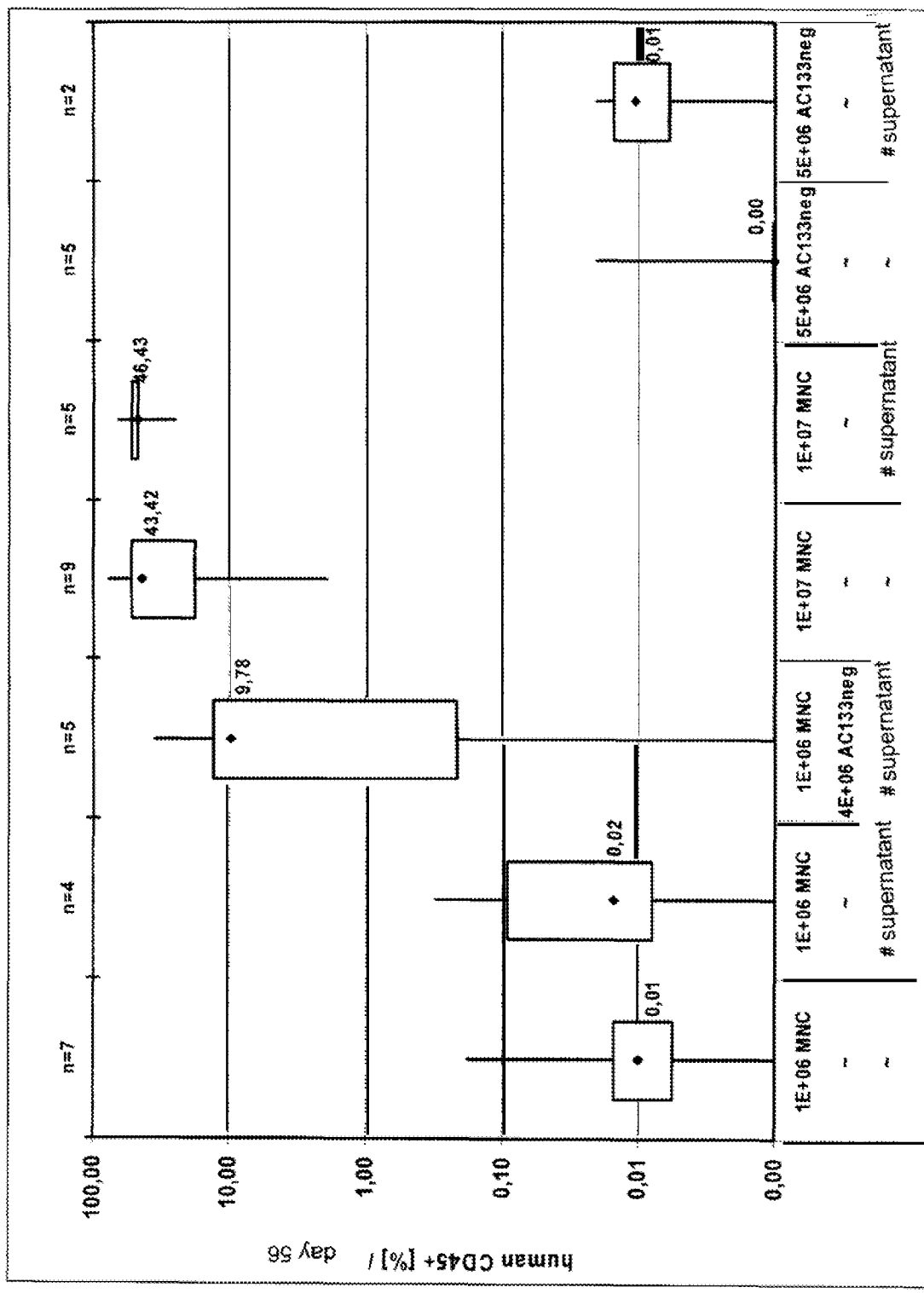
FIG. 6 shows an illustration of the median relative contents of human CD45-positive cells in the bone marrow of humanized mice 8 weeks after transplantation as a function of the applied number of MNC and thus also of the stem cells contained therein, of the use of conditioned supernatant as well as of the use of support cells.

FIG. 6 shows an illustration of the median relative contents of human CD45-positive cells in the bone marrow of humanized mice 8 weeks after transplantation as a function of the applied number of MNC and thus also of the stem cells contained therein, of the use of conditioned supernatant as well as of the use of support cells. The median is illustrated by a diamond and the corresponding numerical values are shown to the right adjacent to the bars, respectively. AC133-negative cell fractions of the mononuclear cells of the umbilical cord blood were used as support cells. AC133 is a surface molecule that is expressed in particular by hematopoietic stem cells (main proportion of these cells carries in turn CD34) as well as by neuronal stem cells and precursor cells of pancreatic cells. This cell fraction had no hematopoietic engraftment of their own in control experiments.

The level of chimerism depends on the number of applied cells (FIG. 6). After administration of $1 \times 10^6$ mononuclear cells (MNC) of the umbilical cord blood without additional conditioning of the recipients with conditioned supernatant only a few animals express an extremely low level chimerism (n=7 [7 animals], left column). The relative proportion of human CD45-positive cells has a median of 0.01% and is thus below the definition of a successful engraftment.

By using the conditioned cell culture supernatant (n=4 [4 animals], 2nd column from the left) the animals express a median of 0.02% of human CD45-positive cells.

However, when administering $1 \times 10^6$ MCN with $4 \times 10^6$ support cells (AC133-negative MNC of the umbilical cord blood) and adding conditioned supernatant, the animals can express successfully a human chimerism (n=5 [5 animals], 3rd column from the left). The median relative proportion of OD45-positive cells is 9.8%.

Control animals that obtained $5 \times 10^6$ support cells (AC133-negative MNC of the umbilical cord blood) showed no human engraftment (n=5 [5 animals], 2nd column from the right). An additional administration of the conditioned supernatant did not enhance the formation of human CD45-positive cells (0.01% CD45-positive cells, n=2 [2 animals], right column).

It is however noteworthy that after administration of $10 \times 10^6$ cells without conditioning with supernatant a significant chimerism was generated in the animals (43.4% CD45-positive cells, n=9 [9 animals]: center column).

However, the extremely low variability of the chimerism generated at a very high level after administration of $10 \times 10^6$ cells under conditioning of the recipients with cell culture supernatant is striking (46.4%, CD45-positive cells, n=5 [5 animals], 3rd column from the right). This low variability in connection with a to stable human chimerism present at a very high level is an ideal prerequisite for further administrations of the humanized mouse (for example, for pathogenesis research).

For assaying the proper function of the formed human B-cells in the mice, human immunoglobulin M (IgM) and immunoglobulin G (IgG) was determined in the serum by means of ELISA. The test shows no cross reactivities with murine immunoglobulin. The detection limit is at 20 ng/ml of immunoglobulin.

By means of human-specific determination of immunoglobulins (Ig), an in vivo reactivity of B-cells in the chimeras was demonstrated after transplantation of $5 \times 10^6$ cells. An IgG production was detected beginning on day 49 at 752 ng/ml with continuous increase to a level of 6,728 ng/ml on day 56, accompanied by IgM production.

For testing the proper function of the human adaptive immune system, a T-cell dependent immunization of the humanized NOD/SCID animals with tetanus toxoid (TT) was done. The immune reactivity was assayed with a human-specific TT-specific antibody assay (IgG, IgM) with ELISA (FIG. 7).

The experiment was carried out in animals that had developed, in accordance with the explained method, a complete human immune system with a relative T-cell proportion >20% (relative proportion CD3-positive cells in the blood on day 56 after transplantation, n=2; T-cell group to the left in FIG. 7). As a control group animals with a relative human T-cell proportion in the blood of <2% was used (B-cell group to the right in FIG. 7, n=6). The immunization was realized respectively intraperitoneally on day 0 (day 0 of the immunization corresponds to day 56 after transplantation), day 14, day 28, day 42 with 50:g of tetanus toxoid, respectively, in GERBU adjuvant 10 (Gerbu, Gaiberg). The antibody formation was measured on day 42 (D 42) after the immunization (corresponds to day 112 after transplantation).

Figure 7:
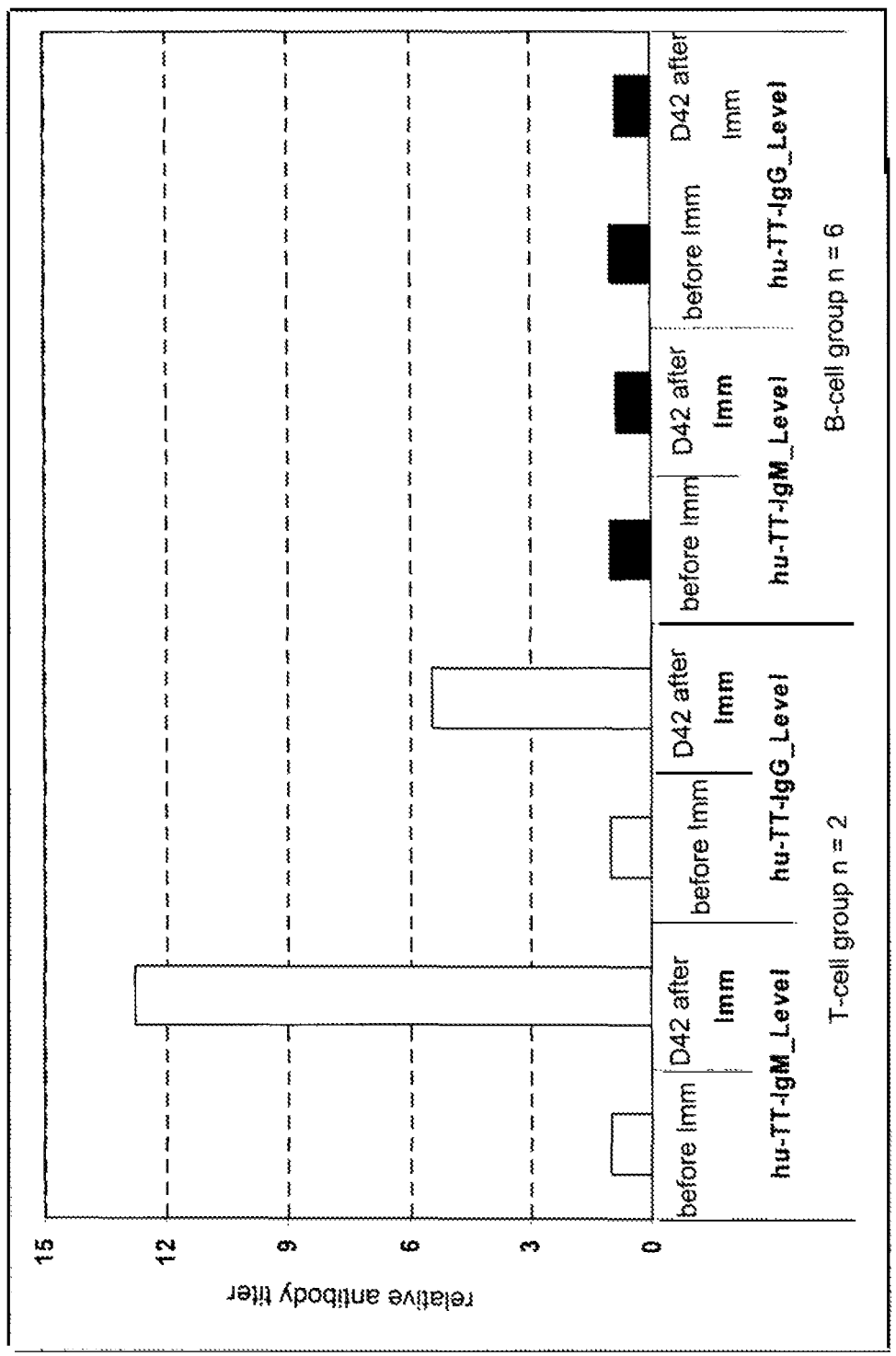
FIG. 7 shows immune reactivity assayed with a human-specific tetanus toxoid (TT)-specific antibody assay (IgG, IgM) with ELISA for testing the proper function of the human adaptive immune system.

FIG. 7 shows that, after the immunization with tetanus toxoid (TT), an antigen-specific immune response in the form of IgM and IgG antibodies is realized in the mice with an established human immune system. In the animals with high T-cell contents (T-cell group—white bars) on day 42 (D 42) after immunization (Imm) tetanus toxoid-specific human IgM (hu-TT-IgM) and IgG (hu-TT-IgG) antibodies can be detected. No TT-specific antibodies were produced in the chimeric animals with a low relative T-cell proportion (B-cell group—black bars).

The human immune system generated in the mice is stable and is still functional far beyond 3 months after transplantation, as has been proven based on a T-cell dependent immune response in the form of human antibodies (FIG. 7).

LIST OF CITED LITERATURE (1) Tornell J, Snaith M. Transgenic systems in drug discovery: from target identification to humanized mice. Drug Discovery Today 2002; 7(8):461-470.
(2) Bolon B. Genetically engineered animals in drug discovery and development; A maturing resource for toxicologic research. Basic & Clinical Pharmacology & Toxicology 2004; 95(4):154-161.
(3) Igney F H, Asadullah K, Zollner T M. Techniques: Species' finest blend-humanized mouse models in inflamma- (4) Traggai E, Chicha L, Mazzucchelli L, Bronz L, Piffaretti J C, Lanzavecchia A et al. Development of a human adaptive immune system in cord blood cell-transplanted mice. Science 2004; 304(5667):104-107.
(5) Kollet O, Peled A, Byk T, Ben Hur H. Greiner D, Shultz L et al. beta 2 microglobulin-deficient (B2m(null)) NOD/SCID mice are excellent recipients for studying human stem cell function. Blood 2000; 95(10):3102-3105.
(6) Rossi M I D, Medina K L, Garrett K, Kolar G, Comp P C, Shultz L D et al. Relatively normal human lymphopoiesis but rap d turnover of newly formed B cells in transplanted nonobese diabetic/SCID mice. Journal of Immunology 2001; 167(6):3033-3042.
(7) Kolar G R, Yokota T. Rossi M I D, Nath S K, Capra J D. Human fetal, cord blood, and adult lymphocyte progenitors have similar potential for generating B cells with a diverse immunoglobulin repertoire. Blood 2004; 104(9): 2981-2987.
(8) Samira S, Ferrand C, Peled A, Nagler A, Tovbin Y. Ben Hur H et al. Tumor Necrosis Factor Promotes Human T-Cell Development in Nonobese Diabetic/Severe Combined Immunodeficient Mice. Stem Cells 2004; 22(6): 1085-1100.
(9) Vallet V, Mauray S, Kindler V, Aubry D, Ruegg M, Cherpillod J et al. Human tonsil implants xenotransplanted in SCID mice display broad lymphocytic diversity and cellular activation profile similar to those in the original lymphoid organ. Xenotransplantation 2005-12(1): 38-48.
(10) Nobuyoshi M, Kusunoki Y, Seyama T, Kodama K, Kimura A, Kyoizumi S. Arrest of human dendritic cells at the CD34(−)/CD4(+)/HLA-DR+ stage in the bone marrow of NOD/SCID-human chimeric mice, Blood 2001; 97(11): 3655-3657.
(11) Cravens P D, Melkus M W, Padgett-Thomas A, Islas-Ohlmayer M, del M, Garcia J V. Development and Activation of Human Dendritic Cells In Vivo in a Xenograft Model of Human Hematopoiesis. Stem Cells 2005; 23(2): 264-278.

LIST OF ABBREVIATIONS

In the description of the invention and in the Figures the following abbreviations are used:
ANG angiogenin
APC allophycocyanin
bFGF basic fibroblast growth factor
CD cluster of differentiation
CFSE carboxyfluorescin succinimidyl ester
DSZM Deutsche Sammlung von Mikroorganismen und Zellkulturen GmbH (German Collection of Microorganisms and Cell Cultures)
EBV Epstein-Barr virus
ELISA enzym linked immuno sorbent assay
HLA human leukocyte antigen
HIV human immunodeficiency virus
HSV human stomatitis virus
hu human
IGF insulin-like growth factor
IL interleukin
IP-10 interferon-(-induced protein 10
BM bone marrow
LPS lipopolysaccharide
MCP-1 monocyte chemoattractant protein-1
MIG monokine-induced by interferon-(
MNC Mononuclear cell
NOD non-obese diabetic
NK natural killer
PC7 phycocyanin 7
PE phycoerythrin
PerCP peridinine chlorophyll protein
RANTES regulated upon activation, normal T-cell expressed and secreted
sCD40L soluble CD40-Ligand
SCID severe-combined-immuno-deficiency
sP selectin soluble platelet selectin
sVCAM-1 vascular cellular adhesion molecule-1
TNF-α tumor necrosis factor-alpha
tPA tissue-type plasminogen activator
VEGF vascular endothelial growth factor

What is claimed is:

1. A method for producing human immune-competent cells in a genetically immunodeficient mouse, wherein the mouse is a NOD mouse or a NOD/SCID mouse, the method comprising:
   a) transplanting an amount of human mononuclear cells (MNC) into the genetically immunodeficient mouse, and
   b) administering to the genetically immunodeficient mouse a conditioned cell culture supernatant of a culture of at least one member of the group consisting of human cell lines, cells and tissue; wherein the conditioned cell culture supernatant contains the factors: interleukin-8 (IL-8), interleukin-6 (IL-6), vascular endothelial growth factor (VEGF), interferon-γ-induced protein 10 (IP-10), monocyte chemoattractant protein-1 (MCP-1), angiogenin (ANG) and tissue-type plasminogen activator (t-PA), each of the factors contained in a concentration of 20 pg/ml to 10 ng/ml, wherein 8 weeks after the transplantation of said MNC, said immunodeficient mouse produces T-cells and B-cells, monocytes, dendritic cells, NK cells, granulocytes, and CD34+ stem cells, wherein the amount of human MNC is sufficient to establish at least 29% T-cells and 20% B-cells of human origin in the spleen of the mouse.

2. The method according to claim 1, wherein the conditioned cell culture supernatant is isolated from cell lines producing cytokines and other molecular mediators.

3. The method according to claim 1, wherein the human MNC are isolated from human bone marrow, mobilized and non-mobilized peripheral blood, umbilical cord blood or umbilical cord tissue.

4. The method according to claim 1, wherein the step a) is carried out 3 to 24 hours after irradiation of the mouse.

5. The method according to claim 1, wherein the step b) is carried out by intravenous or intraperitoneal administration of the conditioned cell culture supernatant.

6. The method according to claim 1, wherein the step b) is carried out in a period of 4 weeks after the step a), beginning with the day when the step a) is carried out.

7. The method according to claim 1, further comprising the step c) of administering support cells that have no hematopoietic potential on their own to the genetically immunodeficient mouse.

8. The method according to claim 1, wherein the conditioned cell culture supernatant contains 500 pg/ml to 10 ng/ml of interleukin-8, 50 pg/ml to 1 ng/ml of interleukin-6, 500 pg/ml to 10 ng/ml of vascular endothelial growth factor (VEGF), 20 pg/ml to 1 ng/ml of interferon-γ-induced protein 10, 500 pg/ml to 10 ng/ml of monocyte chemoattractant protein-1, 20 pg/ml to 1 ng/ml of angiogenin, and 500 pg/ml to 15 ng/ml of tissue-type plasminogen activator.

* * * * *